US012588952B2

(12) United States Patent
Racheli et al.

(10) Patent No.: US 12,588,952 B2
(45) Date of Patent: Mar. 31, 2026

(54) FLEXIBLE MULTI-COIL TRACKING SENSOR

(71) Applicant: BIOSENSE WEBSTER (ISRAEL) LTD., Yokneam (IL)

(72) Inventors: Noam Racheli, Hadera (IL); Matityahu Amit, Cohav-Yair Zur-Yigal (IL); Oleg Dulger, Zichron Yaakov (IL); Itamar Bustan, Zichron Ya'acov (IL); Yoav Pinsky, Beit Keshet (IL); Uriel Hod, Ein Ayala (IL); Helen Wolfson, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 959 days.

(21) Appl. No.: 16/729,313

(22) Filed: Dec. 28, 2019

(65) Prior Publication Data

US 2020/0237459 A1 Jul. 30, 2020

Related U.S. Application Data

(60) Provisional application No. 62/797,118, filed on Jan. 25, 2019, provisional application No. 62/797,091, filed on Jan. 25, 2019.

(51) Int. Cl.
| | |
|---|---|
| *A61B 5/00* | (2006.01) |
| *A61B 5/06* | (2006.01) |
| *A61B 34/20* | (2016.01) |
| *A61B 34/32* | (2016.01) |
| *G06T 7/33* | (2017.01) |
| *G06V 20/64* | (2022.01) |
| *G06V 40/16* | (2022.01) |

(Continued)

(52) U.S. Cl.
CPC .............. *A61B 34/20* (2016.02); *A61B 5/062* (2013.01); *A61B 34/32* (2016.02); *G06T 7/337* (2017.01); *G06V 20/64* (2022.01); *G06V 40/166* (2022.01); *G06V 40/172* (2022.01); *H01F 27/2804* (2013.01); *A61B 2034/2051* (2016.02); *A61B 2034/2065* (2016.02); *A61B 2034/301* (2016.02); *A61B 2034/302* (2016.02); *G06T 2207/30204* (2013.01); *G06V 2201/03* (2022.01)

(58) Field of Classification Search
CPC .... A61B 2034/2051; A61B 2034/2072; H01F 27/2804
See application file for complete search history.

(56) References Cited

U.S. PATENT DOCUMENTS

| | | | | |
|---|---|---|---|---|
| 5,295,482 A | * | 3/1994 | Clare | ................... A61N 1/0492 600/385 |
| 2002/0068890 A1 | * | 6/2002 | Schwenn | .............. A61F 5/0193 602/5 |

(Continued)

OTHER PUBLICATIONS

International Search Report and Written Opinion mailed Apr. 21, 2020 from corresponding PCT Patent Application No. PCT/IB2020/050255.

(Continued)

*Primary Examiner* — Rajeev P Siripurapu
(74) *Attorney, Agent, or Firm* — FBT Gibbons LLP

(57) ABSTRACT

An apparatus includes a plurality of substrates, configured to adhere to a body of a subject via respective pieces of adhesive material, and multiple coils coupled to the substrates, respectively. Other embodiments are also described.

17 Claims, 4 Drawing Sheets

(51) Int. Cl.
   *H01F 27/28*       (2006.01)
   *A61B 34/30*       (2016.01)

(56)           References Cited

U.S. PATENT DOCUMENTS

| | | | |
|---|---|---|---|
| 2003/0144622 A1* | 7/2003 | Kylberg | A61F 5/01 602/41 |
| 2006/0173269 A1* | 8/2006 | Glossop | A61B 5/06 600/407 |
| 2008/0208091 A1* | 8/2008 | Vollbrecht | A61F 5/028 602/19 |
| 2010/0076533 A1* | 3/2010 | Dar | A61N 1/0492 607/115 |
| 2010/0274124 A1 | 10/2010 | Jascob et al. | |
| 2012/0029343 A1 | 2/2012 | Wasson et al. | |
| 2014/0018662 A1 | 1/2014 | Montag | |
| 2014/0031892 A1* | 1/2014 | Mashiach | A61N 1/37229 607/46 |
| 2015/0305612 A1* | 10/2015 | Hunter | A61B 5/062 600/109 |
| 2015/0327948 A1* | 11/2015 | Schoepp | A61B 5/061 600/424 |
| 2017/0181706 A1 | 6/2017 | Montag et al. | |
| 2018/0221566 A1 | 8/2018 | Ohnmacht et al. | |
| 2018/0256110 A1 | 9/2018 | Govari et al. | |

OTHER PUBLICATIONS

U.S. Appl. No. 16/211,594.

* cited by examiner

FLEXIBLE MULTI-COIL TRACKING SENSOR

CROSS-REFERENCE TO RELATED APPLICATIONS

The present application claims the benefit of (i) U.S. Provisional Application 62/797,091, entitled "Registration of frames of reference," filed Jan. 25, 2019, whose disclosure is incorporated herein by reference, and (ii) U.S. Provisional Application 62/797,118, entitled "Flexible multi-coil tracking sensor," filed Jan. 25, 2019, whose disclosure is incorporated herein by reference.

FIELD OF THE INVENTION

The present invention relates to tracking systems for medical procedures, such as otorhinolaryngological surgical procedures.

BACKGROUND

US Patent Application Publication 2010/0274124, issued as U.S. Pat. No. 8,271,069 on Sep. 18, 2012, describes a surgical navigation system for navigating a region of a patient that may include a non-invasive dynamic reference frame and/or fiducial marker, sensor tipped instruments, and isolator circuits. Also methods are provided to determine positions of the dynamic reference frames.

SUMMARY OF THE INVENTION

There is provided, in accordance with some embodiments of the present invention, an apparatus that includes a substrate. The substrate includes a plurality of wider portions, configured to adhere to a body of a subject via respective pieces of adhesive material, and one or more flexible narrower portions. Each of the flexible narrower portions connects a respective pair of successive ones of the wider portions to one another, and is configured to flex in response to movement of any one of the pair. The apparatus further includes multiple coils coupled to the wider portions, respectively.

In some embodiments, the apparatus further includes the pieces of adhesive material.

In some embodiments, the substrate includes a polyimide.

In some embodiments, the wider portions consist of two wider portions.

In some embodiments, the wider portions include three wider portions.

In some embodiments, in an absence of any force applied to the substrate, the coils are non-collinear.

In some embodiments, each of the narrower portions is U-shaped.

In some embodiments, the coils are planar.

In some embodiments, the coils include respective traces that coat the substrate.

There is further provided, in accordance with some embodiments of the present invention, an apparatus that includes a plurality of substrates, configured to adhere to a body of a subject via respective pieces of adhesive material, and multiple coils coupled to the substrates, respectively.

In some embodiments, the apparatus further includes the pieces of adhesive material.

In some embodiments, the substrates consist of two substrates.

In some embodiments, the substrates include three substrates.

In some embodiments, the coils are planar.

In some embodiments, the apparatus further includes one or more flexible connectors, each of which:

connects a respective pair of successive ones of the substrates to one another, and is configured to flex in response to movement of any one of the pair.

In some embodiments, when no force is applied to any one of the substrates, the coils are non-collinear.

In some embodiments, the connectors include respective springs.

In some embodiments, the connectors include respective elastic strips.

There is further provided, in accordance with some embodiments of the present invention, a method for facilitating surgery on a portion of a body of a subject. The method includes receiving respective signals that are induced, by a magnetic field, in a plurality of coils that are coupled to the portion of the body of the subject. The method further includes, at an initial time, based on the signals, calculating initial relative poses of the coils with respect to each other. The method further includes, subsequently to the initial time, repeatedly, based on the signals, ascertaining that the coils are at the initial relative poses, and, in response to ascertaining that the coils are at the initial relative poses, calculating a pose of the portion of the body and, in response to the calculated pose, performing an action to facilitate the surgery. The method further includes, at a subsequent time, based on the signals, ascertaining that the coils are not at the initial relative poses, and, in response to ascertaining, at the subsequent time, that the coils are not at the initial relative poses, stopping the surgery.

In some embodiments, the surgery is performed by a robot using a tool, performing the action includes communicating an instruction to the robot to move the tool, and stopping the surgery includes stopping the surgery by instructing the robot to stop performing the surgery.

In some embodiments, the method further includes, in response to ascertaining that the coils are not at the initial relative poses, generating an alert indicating that the coils are not at the initial relative poses.

In some embodiments, the surgery is performed using a tool, and performing the action includes superimposing an icon representing the tool over a scan of the portion of the body of the subject.

In some embodiments, stopping the surgery includes stopping the surgery by generating an alert indicating that the coils are not at the initial relative poses.

The present invention will be more fully understood from the following detailed description of embodiments thereof, taken together with the drawings, in which:

DETAILED DESCRIPTION OF EMBODIMENTS

Glossary

Figure 1:
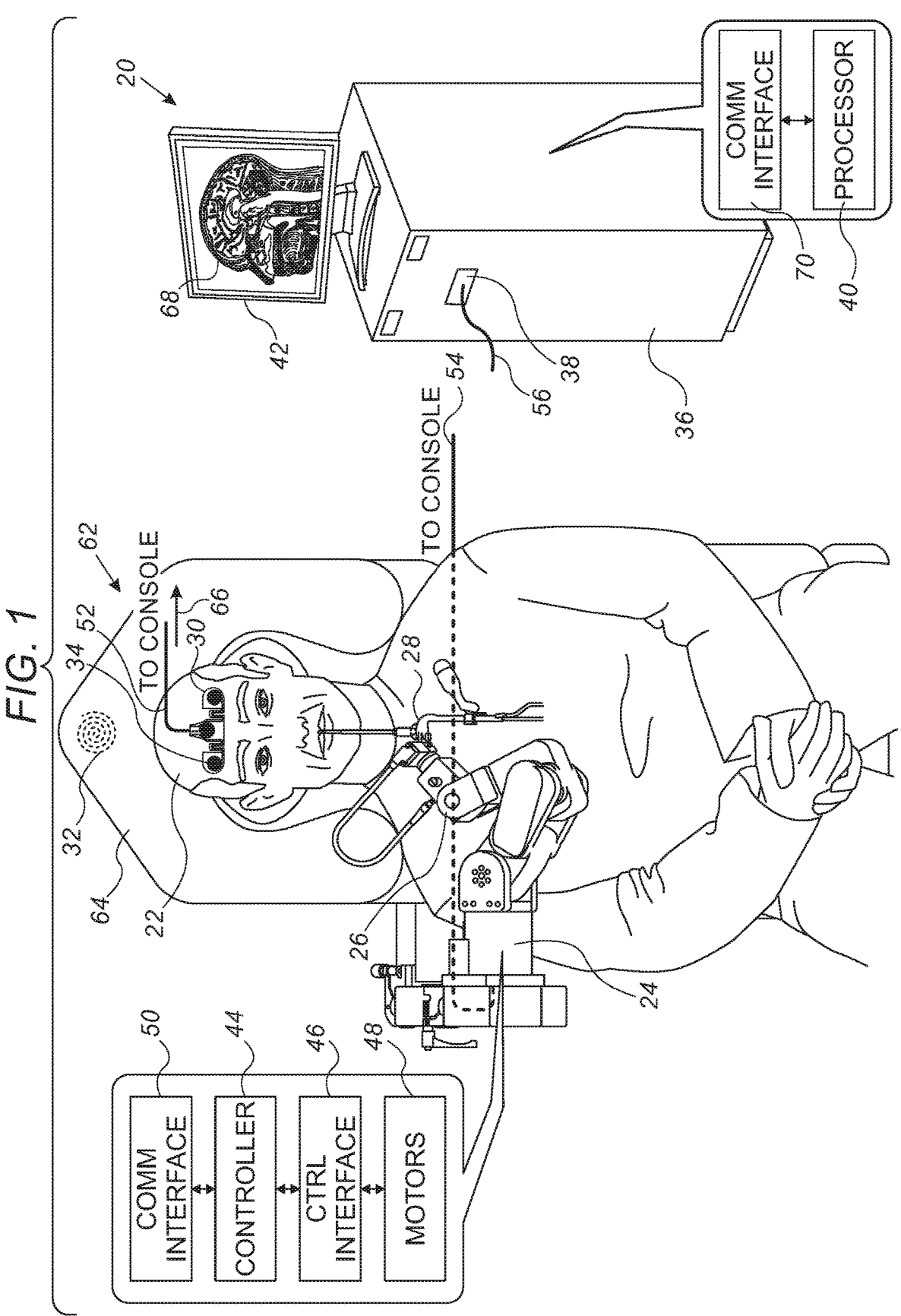
FIG. 1 is a schematic illustration of a system for performing robotic surgery on a subject, in accordance with some embodiments of the present invention.

In the context of the present application, including the claims, the "pose" of an object refers to the combination of the location of the object and the orientation of the object. Thus, for example, in a three-dimensional setting, the pose of an object may be described by a location vector (x, y, z), which describes the location of the object, together with an orientation vector (x', y', z'), which describes the orientation of the object. (Typically, the orientation vector is normalized so as to be of unit length.)

Overview

Some surgical procedures utilize an electromagnetic tracking system to track the pose of the subject, and/or of at least one surgical tool, during the procedure. Such a tracking system may comprise a plurality of generating coils located at different respective positions, along with one or more sensing coils that function as tracking sensors. The generating coils generate magnetic fields at different respective frequencies. As the sensing coils move in the presence of this composite magnetic field, the voltages induced in the sensing coils vary as a function of their respective poses. Hence, based on these induced voltages, a processor may ascertain the respective poses of the sensing coils, and hence, the pose of the subject or of the tool.

For example, for an otorhinolaryngological surgical procedure, a tracking sensor, comprising a plurality of coils, may be coupled to the subject's forehead. Prior to the procedure, the pose of the tracking sensor relative to the skull of the subject may be recorded. Subsequently, during the procedure, based on the voltages induced in the tracking sensor, the pose of the tracking sensor may be tracked. Based on the pose of the tracking sensor, the processor may track the pose of the subject's skull, provided that the sensor does not move relative to the skull.

One possible embodiment of the aforementioned tracking sensor is a triple-axis sensor (TAS), comprising a rigid unit of three barrel coils oriented along different respective axes. A disadvantage of such an embodiment, however, is that shifting of the subject's skin may cause all three coils to move in tandem. If such movement occurs, the processor may incorrectly compute the pose of the skull.

Hence, instead of a TAS, embodiments of the present invention provide a flexible multi-coil tracking sensor, comprising three coils—which may be referred to as single-axis sensors (SASs)—that are variably disposed with respect to each other by virtue of the flexibility of the sensor. Prior to the procedure, the sensor is coupled to the subject's forehead, and the respective poses of the coils relative to each other are recorded. Subsequently, during the procedure, the processor monitors the relative poses of the coils. If any one of the relative poses changes (i.e., if the position and/or orientation of one coil relative to another coil changes), the processor generates an alert indicating a possible shift of the subject's skin. In response to the alert, the operating physician may reverse the shift.

In some embodiments, the tracking sensor comprises a flexible electrically-insulative substrate, such as a flexible polyimide substrate, comprising three wider portions that are connected to each other by two flexible narrower portions. The coils are formed from respective traces that coat the wider portions, respectively. (The traces may be formed, for example, by an etching or sputtering procedure.) Whereas the wider portions are coupled to the subject's forehead using a suitable adhesive (e.g., double-sided medical tape), the narrower portions are not. Hence, as the skin of the subject shifts, the shape of the narrower portions may change, such that the relative poses of the coils may change.

In other embodiments, the sensor comprises three electrically-insulative substrates, a respective coil being coupled to each of the substrates. In some such embodiments, the substrates are connected to each other by elastic bands or strips, or by springs.

In addition to otorhinolaryngological procedures, the sensors described herein may be used for spinal procedures, thoracic procedures, or any other suitable type of procedure. For these other procedures, the sensors may be coupled to the subject's back or chest, or to any other suitable portion of the subject's body.

System Description

Reference is initially made to FIG. 1, which is a schematic illustration of a system 20 for performing robotic surgery on a subject 22, in accordance with some embodiments of the present invention.

System 20 comprises a surgical robot 24, comprising an arm 26 and a controller 44. Controller 44 is configured to control arm 26, typically by operating one or more motors 48 via a control (CTRL) interface 46. Arm 26 is configured to hold a tool 28, such as a suction tool or an endoscope. Thus, by moving arm 26, controller 44 may position tool 28 at any suitable pose within the body of subject 22. For example, controller 44 may position the distal end of an endoscope within the subject's nasal cavity, such that the endoscope may acquire images of the cavity.

System 20 further comprises a processor 40, which is typically located in a console 36. Controller 44 operates arm 26 in response to instructions received from processor 40.

A cable 54, which runs from console 36 to robot 24, comprises electrical wiring that carries power to the robot. Controller 44 exchanges communication with processor 40 via a communication (COMM) interface 50, which may comprise any suitable circuitry and/or other hardware. In some embodiments, communication interface 50 is a wired communication interface; in such embodiments, cable 54 may comprise wiring that carries communication signals between the controller and the processor. In other embodiments, the communication interface is a wireless communication interface.

Cable 54 is connected to console 36 via a first electrical interface 38 (comprising, for example, a port or socket), and to robot 24 via a second electrical interface. In some embodiments, the console-facing end of cable 54 is bundled, together with the respective ends of the various other cables described herein, in a central cable 56.

System 20 further comprises an electromagnetic tracking system 62. Tracking system 62 comprises a subject-tracking sensor 30, which is coupled to the subject's head (e.g. to the subject's forehead) or to any other suitable portion of the subject's body. Sensor 30 comprises a plurality of coils 34, which are connected to console 36 via at least one cable 52 that is connected to electrical interface 38. As further described below with reference to FIGS. 2A-B and FIG. 3, coils 34 are coupled to the subject such that shifting of the subject's skin may cause any one of the coils to change its pose relative to the other coils.

Tracking system 62 further comprises a plurality of (e.g., between 10 and 20) generating coils 32, which are disposed at different respective positions in the vicinity of subject 22, e.g., within an emitter pad 64 positioned underneath and/or near the subject's head. (For ease of illustration, only one stationary coil 32 is shown in FIG. 1.) During the surgery, alternating currents are passed through generating coils 32 (or through subsets of the generating coils) at different respective frequencies, such that the generating coils generate a magnetic field at the different frequencies. The magnetic field induces signals 66 in coils 34. Signals 66, which are carried to console 36 by cable 52, are received by the processor via electrical interface 38.

Tracking system 62 further comprises at least one tool-tracking sensor (not shown), comprising one or more coils, which is coupled to tool 28 and/or to arm 26. The tool-tracking sensor also outputs one or more signals responsively to the generated magnetic field. Based on these signals, the processor calculates the pose of the tool.

As further described below with reference to FIG. 4, based on signals 66, processor 40 computes the relative poses of the coils with respect to each other. If the relative poses have not changed from their initial values, the processor, based on signals 66, calculates the pose of the subject's head. Based on the pose of the subject's head and the pose of the tool, the processor controls robot 24 so as to achieve the desired pose of the tool relative to the subject's head. On the other hand, if the relative poses have changed, the processor stops the surgery, since the change in the relative poses indicates that the pose of the subject's head cannot be accurately calculated.

In alternative embodiments, coils 34, and the coils belonging to the tool-tracking sensor, function as generating coils, which induce signals in coils 32. Based on these induced signals, the processor calculates the pose of the subject's head and the pose of the tool.

In addition to processor 40 and electrical interface 38, console 36 typically comprises a wired or wireless communication (COMM) interface 70 for communicating with robot 24. Typically, the console further comprises a monitor 42, which is configured to display a preoperative volumetric scan 68, such as a computerized tomography (CT) scan, of the subject's head. Using monitor 42, a physician may visually track the movement of tool 28 during the procedure, and/or specify a target pose for the tool, e.g., by drawing or moving an icon superimposed over preoperative scan 68.

Notwithstanding the particular surgical application shown in FIG. 1, it is noted that sensor 30 may be used for any suitable robotic or manual surgical application.

In general, processor 40 may be embodied as a single processor, or as a cooperatively networked or clustered set of processors. In some embodiments, the functionality of processor 40, as described herein, is implemented solely in hardware, e.g., using one or more Application-Specific Integrated Circuits (ASICs) or Field-Programmable Gate Arrays (FPGAs). In other embodiments, the functionality of processor 40 is implemented at least partly in software. For example, in some embodiments, processor 40 is embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Figures 2A, 2B:
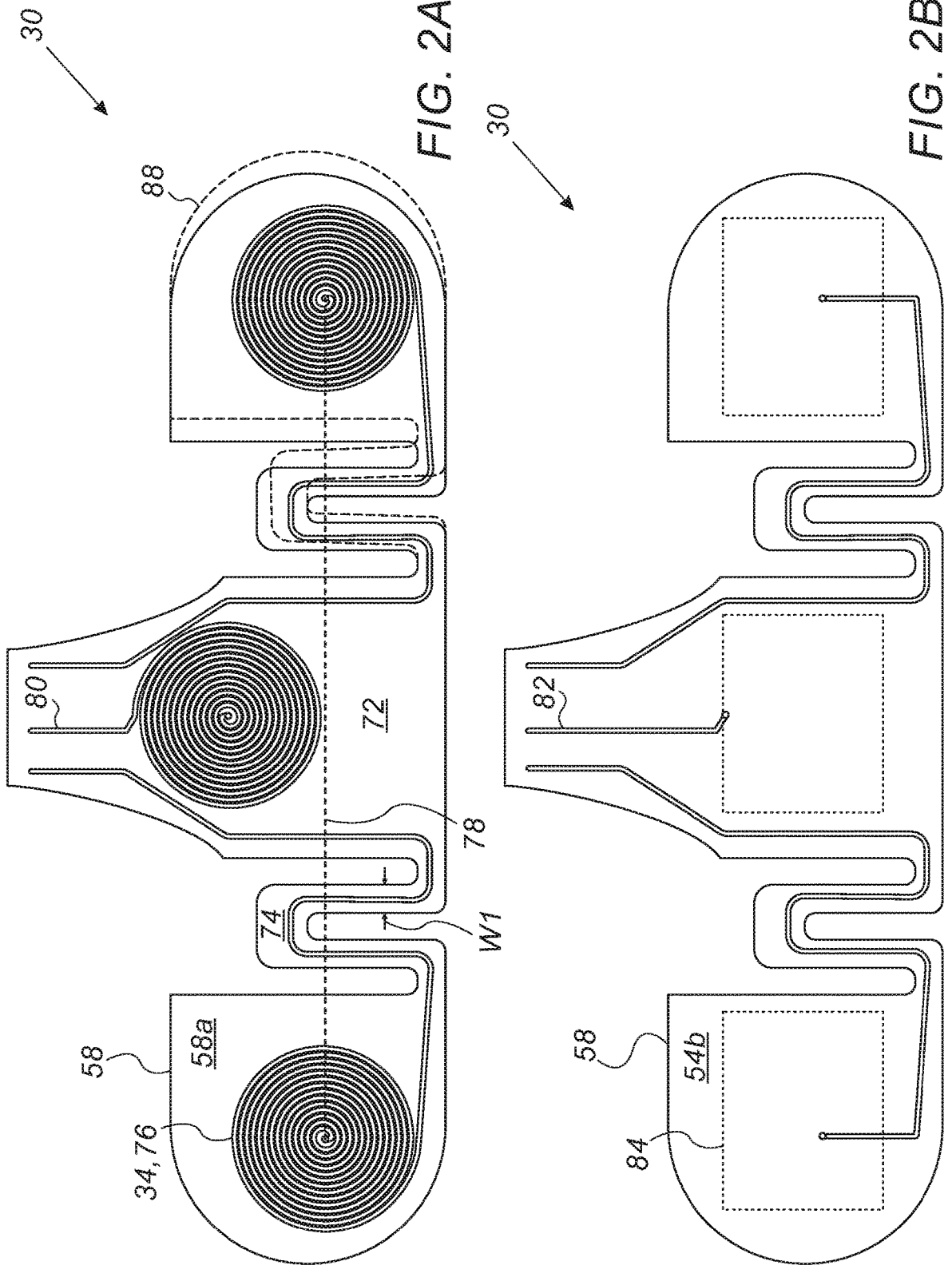
FIG. 2A is a schematic illustration of a first surface of a sensor, in accordance with some embodiments of the present invention.
FIG. 2B is a schematic illustration of a second surface of a sensor, in accordance with some embodiments of the present invention.

Reference is now made to FIG. 2A, which is a schematic illustration of a first surface of sensor 30, in accordance with some embodiments of the present invention. Reference is additionally made to FIG. 2B, which is a schematic illustration of a second surface of sensor 30, which is opposite the first surface, in accordance with some embodiments of the present invention.

Sensor 30 comprises a substrate 58, comprising a plurality of (e.g., two or three) wider portions 72, and one or more flexible narrower portions 74, each of which connects a respective pair of successive wider portions 72 to one another. For example, for embodiments comprising three wider portions as in FIGS. 2A-B, substrate 58 comprises two narrower portions 74: one that connects the left and middle wider portions to one another, and another that connects the middle and right wider portions to one another.

Coils 34 are coupled to the wider portions, respectively, on the first surface 58a of the substrate. Typically, as in FIG. 2A, the coils are planar. In other embodiments, at least one of the coils is a barrel coil.

Typically, for embodiments comprising three or more coils, the coils are non-collinear in the absence of any force applied to substrate 58. In other words, when the substrate is in its default, resting state, the center of at least one coil does not lie on the (hypothetical) line 78 that joins the respective centers of at least two other coils to one another. This property may facilitate calculating the pose of the subject's head from the respective poses of the coils.

In some embodiments, substrate 58 comprises a polyimide, or any other electrically-insulative material on which traces may be formed. In such embodiments, coils 34 may comprise respective traces 76 that coat the substrate. Each trace 76 comprises a terminal 80 that connects to a wire that passes through cable 52 (FIG. 1). Typically, a via passing through substrate 58 connects the other terminal of trace 76 to another trace 82 on the second surface 58b of the substrate. Trace 82 connects to another wire that passes through cable 52.

In some embodiments, sensor 30 further comprises multiple pieces 84 of adhesive material, configured to adhere the wider portions to the body of the subject. (Typically, pieces 84 adhere to second surface 58b.) In other embodiments, the pieces of adhesive material are provided separately from sensor 30. In such embodiments, prior to the surgery, the pieces of adhesive material are stuck to the wider portions, and the wider portions are then adhered to the subject's skin via the pieces of adhesive material. Subsequently to the surgery, the pieces of adhesive material may be removed from the sensor, and the sensor may then be reused for another surgical procedure.

Advantageously, each narrower portion 74 is configured to flex in response to movement of any one of the two wider portions to which the narrower portion is connected. As a result of this flexion, the relative poses of the coils may change.

For example, FIG. 2A illustrates, by means of a dashed outline 88, a hypothetical rightward movement of the right wider portion of the substrate, e.g., by virtue of the skin of the subject shifting while the sensor is coupled to the subject. In response to this movement, the narrower portion that connects the right wider portion to the middle wider portion flexes, such that the distance between the right coil and the middle coil increases.

In general, narrower portions 74 may have any shape suitable for facilitating the flexion described herein. For example, as shown in FIGS. 2A-B, each of the narrower portions may be U-shaped. Alternatively, at least one of the narrower portions may be sinusoidal-shaped or arc-shaped. In some embodiments, the width W1 of the narrower portions is less than 30, 20, 10, or 5 mm. Alternatively or additionally, the width of the wider portions may be greater than (e.g., at least 10%, 20%, or 30% greater than) W1.

Typically, at least part of the first surface of substrate 58 is covered (e.g., by a plastic cover), such that coils 34 are hidden from view. Alternatively or additionally, the second surface of substrate 58 may be covered (in addition to the cover provided by the adhesive), such that traces 82 are hidden from view. For example, traces 82 may be covered by a layer of foam and/or any other electrically-insulative material.

Figure 3:
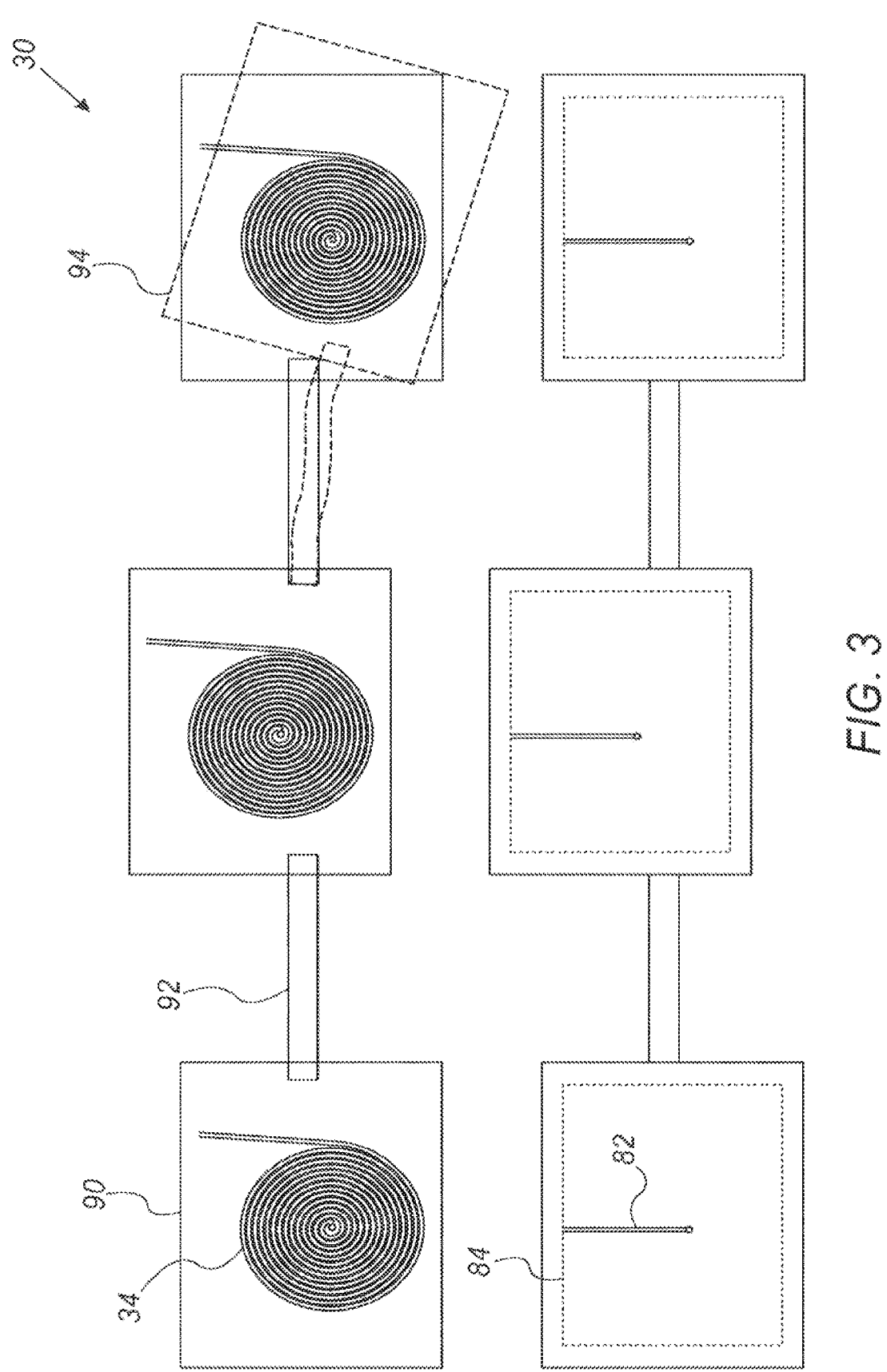
FIG. 3 is a schematic illustration of a sensor, in accordance with some embodiments of the present invention.

Reference is now made to FIG. 3, which is a schematic illustration of sensor 30, in accordance with other embodiments of the present invention. (FIG. 3 shows both the first and second surfaces of the sensor.)

In some embodiments, instead of a single substrate, sensor 30 comprises a plurality of (e.g., two or three) substrates 90, a respective coil 34 being coupled to each substrate 90. (Typically, for embodiments comprising three or more coils, the coils are non-collinear.) Multiple pieces 84 of adhesive material, which may be provided together with or separately from the substrates, adhere the substrates to the body of the subject. As in FIGS. 2A-B, the first surface and/or second surface of sensor 30 may be covered, such that coils 34 and/or traces 82 are hidden from view.

In some embodiments, substrates 90 are not connected to each other. In other embodiments, sensor 30 comprises one or more flexible connectors 92, such as springs or elastic strips or bands, each of which connects a respective pair of successive substrates to one another. Connectors 92 function analogously to narrower portions 74 (FIGS. 2A-B), in that each connector is configured to flex in response to movement of any one of the substrates to which the connector is connected. For example, FIG. 3 shows, by means of a dashed outline 94, a hypothetical clockwise rotation of the right substrate, which, by virtue of the flexibility of the connecting connector, causes a change in the pose of the right coil relative to the middle coil.

It is noted that an advantage of connecting substrates 90 to each other, or placing the coils on a single substrate as in FIGS. 2A-B, is that sensor 30 is easier to handle.

Figure 4:
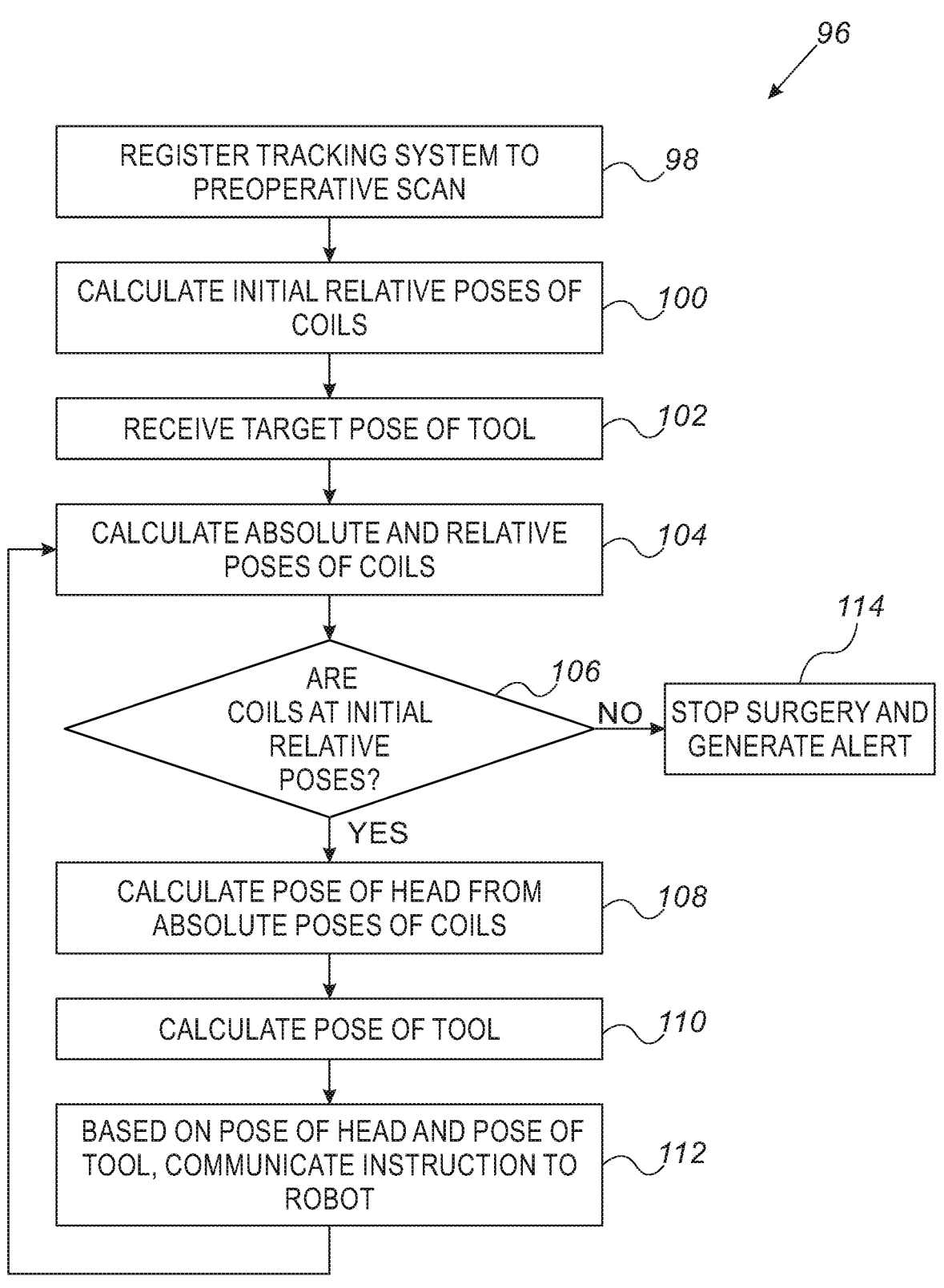
FIG. 4 is a schematic illustration of an example algorithm for facilitating robotic surgery, in accordance with some embodiments of the present invention.

Reference is now made to FIG. 4, which is a schematic illustration of an example algorithm 96 for facilitating robotic surgery, in accordance with some embodiments of the present invention. Algorithm 96 is executed by processor 40 (FIG. 1).

Algorithm 96 begins with a registering step 98, at which the processor registers the tracking system to preoperative scan 68 (FIG. 1). For example, to register the tracking system to a scan of the subject's head, the physician may move a coil, which is disposed at the distal tip of a rod, across the subject's face. As the coil is moved across the face, the processor may repeatedly calculate the position of the coil, thus acquiring a point cloud in the coordinate system of the tracking system. Subsequently, the processor may use any suitable algorithm, such as the Iterative Closest Point (ICP) algorithm, to find the transformation that best maps the point cloud to the surface of the scan that represents the subject's face.

Subsequently, as described above with reference to FIG. 1, the processor continuously receives signals 66, which are induced in coils 34, along with the signals that are induced in the tool-tracking sensors. Based on these signals, the processor performs the steps described below.

In particular, at an initial time, the processor, at an initial-pose-calculating step 100, calculates the initial relative poses of the coils with respect to each other. In other words, based on signals 66, the processor calculates the respective poses of the coils, and then derives the initial relative poses from the respective poses. For example, if the pose (or "absolute pose") of one coil is $\{(x,y,z), (x',y',z')\}$, where $(x,y,z)$ is the position of the coil and $(x',y',z')$ is the orientation of the coil, and the pose of another coil is $\{(a,b,c), (a',b',c')\}$, the processor may calculate the relative pose of the first coil with respect to the second coil as $\{((x-a),(y-b),(z-c)),((x'-a'),(y'-b'),(z'-c'))\}$.

Next, at a target-pose-receiving step 102, the processor receives the target pose of the tool from the physician. For example, as described above with reference to FIG. 1, the processor may receive the position of an icon superimposed over the preoperative scan. Based on the registration that was performed at registering step 98, the processor transforms this location to the coordinate system of the tracking system.

(It is noted that registering step 98, initial-pose-calculating step 100, and target-pose-receiving step 102 may alternatively be performed in any other order.)

Subsequently to the initial time, the processor repeatedly ascertains that the coils are at the initial relative poses, and, in response thereto, controls robot 24 (FIG. 1).

More specifically, the processor first calculates the absolute and relative poses of the coils, at a coil-pose-calculating step 104. In other words, as described above with respect to initial-pose-calculating step 100, the processor calculates the absolute poses of the coils from signals 66, and then calculates the relative poses from the absolute poses.

Next, at a checking step 106, the processor checks whether the coils are at the initial relative poses with respect to each other. If yes, the processor, at a head-pose-calculating step 108, calculates the pose of the head from the absolute poses of the coils, based on the registration that was obtained at registering step 98. Additionally, subsequently or prior to head-pose-calculating step 108, the processor calculates the pose of the tool based on the signal from the tool-tracking sensor, at a tool-pose calculating step 110.

Next, based on the pose of the head and the pose of the tool, the processor performs an action to facilitate the surgery. For example, in some embodiments, at an instruction-communicating step 112, the processor communicates an instruction to the robot to move the tool. In particular, the processor, based on the current pose of the head and pose of the tool, calculates a small target change in the pose of the tool. The processor then communicates the target change to the robot, and the robot, in response thereto, moves the tool by the target change. In this manner, the tool is incrementally moved toward the target pose.

(Typically, the target change must be specified relative to the robot's coordinate system, such that the processor must register the tracking system to the robot's coordinate system. This may be done, for example, using the ICP algorithm, or using alternate techniques described in U.S. application Ser. No. 16/211,594, whose disclosure is incorporated herein by reference.)

Alternatively or additionally, based on the current pose of the head and pose of the tool, the processor may superimpose an icon, which represents the tool, over preoperative scan 68, so as to indicate the pose of the tool relative to that of the head. Thus, the physician may track the progress of the surgery, and, for surgery that is performed manually, navigate the tool toward the target pose.

Alternatively or additionally, based on the current pose of the head and pose of the tool, the processor may generate an alert if the tool is within a certain threshold distance of internal tissue of the subject.

On the other hand, if the processor ascertains at checking step 106, at any time, that the coils are not at the initial relative poses, the processor does not allow the robot to continue the surgery. Rather, in response to ascertaining that the coils are not at the initial relative poses, the processor instructs the robot to stop performing the surgery, at a surgery-stopping step 114. Typically, at surgery-stopping step 114, the processor also generates an alert indicating that the coils are not at the initial relative poses.

Similarly, for manually-performed surgery, if the processor ascertains that the coils are not at the initial relative poses, the processor may stop the surgery by generating an alert indicating that the coils are not at the initial relative poses, such that the physician stops performing the surgery.

In response to the aforementioned alert, the physician may shift the skin of the subject such that the coils return to their initial relative poses. Subsequently, after verifying, at checking step 106, that the coils are at their initial relative poses, the processor may resume the surgery. Alternatively, the processor may reregister the tracking system to the preoperative scan, replace the initial relative poses of the coils with the new relative poses, and then resume the surgery. (In view of the above, it is noted that, in the context of the present application, including the claims, the word "stop" may indicate a temporary stopping, or "pausing.")

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   (a) a substrate, comprising:
      (i) a plurality of wide portions, configured to adhere to a body of a subject via respective pieces of adhesive material, and
      (ii) one or more flexible narrow portions, each flexible connector having a U-shape profile formed from a first linear section, a second linear section, and a connecting section coupling the first and second linear sections, each of which:
         is narrower than and connects a respective pair of successive ones of the wide portions to one another, and
         is configured to flex in response to movement of any one of the pair;
   (b) a plurality of coils, each coil of the plurality of coils being coupled to a respective wide portion of the plurality of wide portions;

(c) a plurality of terminals, each terminal of the plurality of terminals extending from a respective coil of the plurality of coils, each terminal extending from a respective coil and into a common wide portion of the plurality of wide portions, at least one terminal of the plurality of terminal extending though a respective flexible narrow portion of the one or more flexible narrow portions; and
   (d) a processor configured to:
      (i) calculate an initial relative pose of the plurality of coils,
      (ii) calculate a subsequent relative pose of the plurality of coils, and
      (iii) generate an alert if the subsequent relative pose of the plurality of coils deviates from the initial relative pose of the plurality of coils.

2. The apparatus according to claim 1, further comprising the pieces of adhesive material.

3. The apparatus according to claim 1, the substrate comprising a polyimide.

4. The apparatus according to claim 1, the plurality of wide portions comprising a first wide portion and a second wide portion.

5. The apparatus according to claim 1, the plurality of wide portions comprising a first wide portion, a second wide portion, and a third wide portion.

6. The apparatus according to claim 5, the plurality of coils being non-colinear with respect to each other in an absence of any force applied to the substrate.

7. The apparatus according to claim 1, each coil of the plurality of coils being planar.

8. The apparatus according to claim 1, each coil of the plurality of coils comprising respective traces that coat the substrate.

9. Apparatus, comprising:
   (a) a plurality of substrates, configured to adhere to a body of a subject via respective pieces of adhesive material;
   (b) one or more flexible connectors coupled to and extending between adjacent substrates of the plurality of substrates, each flexible connector of the one or more flexible connectors being configured to flex in response to movement of the plurality of substrates relative to each other, each flexible connector having a U-shape profile formed from a first linear section, a second linear section, and a connecting section coupling the first and second linear sections;
   (c) a plurality of coils, each coil of the plurality of coils being coupled to a respective substrate of the plurality of substrates; and
   (d) a plurality of terminals, each terminal of the plurality of terminals extending from a respective coil into a common substrate of the plurality of substrates, at least one terminal of the plurality of terminals extends through a flexible connector of the one or more flexible connectors to extend into the common substrate of the plurality of substrates.

10. The apparatus according to claim 9, further comprising the pieces of adhesive material.

11. The apparatus according to claim 9, the plurality of substrates comprise a first substate and a second substrate.

12. The apparatus according to claim 9, the plurality of substrates comprising a first substrate, a second substrate, and a third substrate.

13. The apparatus according to claim 9, the plurality of coils being planar.

14. The apparatus according to claim 9, further comprising one or more flexible connectors, each of which:

connects a respective pair of successive ones of the
    substrates to one another, and is configured to flex in response to movement of any one
    of the pair.

15. The apparatus according to claim 14, the plurality of
coils being non-colinear with respect to each other when no
force is applied to any one of the substrates.

16. The apparatus according to claim 14, the connectors
comprising respective springs.

17. The apparatus according to claim 14, the connectors
comprising respective elastic strips.

\* \* \* \* \*